US011247882B2

(12) United States Patent
Yu

(10) Patent No.: US 11,247,882 B2
(45) Date of Patent: Feb. 15, 2022

(54) ANTI-FALL MECHANISM FOR LIFTING EQUIPMENT

(71) Applicant: SHANGHAI UNITED IMAGING HEALTHCARE CO., LTD., Shanghai (CN)

(72) Inventor: Yinmin Yu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 16/932,715

(22) Filed: Jul. 18, 2020

(65) Prior Publication Data

US 2020/0346905 A1    Nov. 5, 2020

Related U.S. Application Data

(63) Continuation of application No. 15/692,177, filed on Aug. 31, 2017, now Pat. No. 10,717,635.

(30) Foreign Application Priority Data

Aug. 23, 2017  (CN) .......................... 201710731569.9

(51) Int. Cl.
  *B66D 5/30* (2006.01)
  *B66D 5/16* (2006.01)
  *B66D 1/36* (2006.01)
  *A61B 6/00* (2006.01)
  *B66D 5/22* (2006.01)
  *E04G 3/32* (2006.01)

(52) U.S. Cl.
  CPC .............. *B66D 5/30* (2013.01); *A61B 6/4435* (2013.01); *B66D 1/36* (2013.01); *B66D 5/16* (2013.01); *B66D 5/22* (2013.01); *E04G 3/32* (2013.01)

(58) Field of Classification Search
  CPC .......... A61B 6/4435; B66D 1/36; B66D 5/16; B66D 5/22; B66D 5/30; E04G 3/32
  See application file for complete search history.

(56) References Cited

U.S. PATENT DOCUMENTS

| 4,279,329 A | 7/1981 | Gehron |
| 6,142,667 A | 11/2000 | Pattee |
| 2009/0120219 A1 | 5/2009 | Lykkegaard |

FOREIGN PATENT DOCUMENTS

| CN | 2900934 Y | 5/2007 |
| CN | 201125996 Y | 10/2008 |
| CN | 202301806 U | 7/2012 |
| CN | 101737611 B | 12/2012 |

(Continued)

OTHER PUBLICATIONS

First Office Action in Chinese Application No. 201710731569.9 dated Aug. 28, 2018, 12 pages.

*Primary Examiner* — Mark R Gaworecki
(74) *Attorney, Agent, or Firm* — Metis IP LLC

(57) ABSTRACT

A lifting equipment is provided. The lifting equipment may include a working assembly, a safety assembly, and a shaft assembly. The working assembly may include a working fastener. The working fastener may be spirally connected to the shaft assembly. When the shaft assembly rotates the working fastener may move along the shaft assembly. The safety assembly may comprise a limiting component. The limiting component may be connected to the working fastener. A portion of the safety assembly may be in located a space between the limiting component and the working assembly.

20 Claims, 7 Drawing Sheets

(56) References Cited

FOREIGN PATENT DOCUMENTS

| | | |
|---|---|---|
| CN | 202946633 U | 5/2013 |
| CN | 204372078 U | 6/2015 |
| CN | 205780672 U | 12/2016 |
| GB | 925995 A | 5/1963 |

ANTI-FALL MECHANISM FOR LIFTING EQUIPMENT

CROSS-REFERENCE TO RELATED APPLICATIONS

This application is a continuation of U.S. application Ser. No. 15/692,177, filed on Aug. 31, 2017, which in turn claims priority of Chinese Patent Application No. 201710731569.9 filed on Aug. 23, 2017, the entire contents of each of which are hereby incorporated by reference.

TECHNICAL FIELD

The present disclosure generally relates to an anti-fall mechanism for lifting equipment, and more particularly, to an anti-fall mechanism for a C-arm device with a lifting component.

BACKGROUND

At present, many lifting components in devices, e.g., medical devices, use a shaft-driving mechanism. However, a shaft-driving mechanism is generally equipped with only one fastener and one shaft. The risk of malfunction of the fastener increases when the load on the fastener is abnormal, or the fastener itself is defective. When the fastener is disengaged from the shaft, a load lifting mechanism in the lifting component and/or an object being lifted by the load lifting mechanism are likely to fall, compromising the service life and/or safety of the lifting component and/or the device incorporating the same.

SUMMARY

In accordance with some embodiments of the disclosed subject matter, a medical device and lifting structures are provided.

One aspect of the present disclosure relates to a system. The system may include a safety assembly, a shaft assembly, and a load lifting mechanism. The safety assembly may be configured to prevent the load lifting mechanism from falling when the working assembly fails. The safety assembly may be coupled to the load lifting mechanism. The working assembly may be connected to the shaft assembly. The safety assembly may be coupled to the load lifting mechanism. The working assembly may be connected to the shaft assembly. The safety assembly may be connected to the shaft assembly. The safety assembly may include a safety fastener and a limiting component. Projection of the safety fastener and projection of the limiting component in a plane perpendicular to the shaft assembly at least partially overlap.

In some embodiments, the working assembly may include a working fastener configured to drive the load lifting mechanism to move along the shaft assembly when the working fastener is engaged with the shaft assembly.

In some embodiments, the safety fastener configured to support the load lifting mechanism when the working fastener is disengaged from the shaft assembly.

In some embodiments, the safety fastener may be a safety nut, and the working fastener may be a working nut.

In some embodiments, the shaft assembly may be a screw thread rod or a ball screw rod.

In some embodiments, the load lifting mechanism may include a first fastener surface and a second fastener surface. The working fastener may include a first connecting portion and a first fastener portion. The first connecting portion may be connected to the shaft assembly. The first fastener portion may be connected to the first fastener surface. The safety fastener may include a second connecting portion. The second connecting portion may be connected to the shaft assembly.

In some embodiments, the limiting component may be connected to the load lifting mechanism. The safety assembly may include a housing between the limiting component and the second fastener surface, wherein the housing accommodates at least a part of a second fastener portion of the safety fastener. The safety assembly may include a locking component. The safety assembly may include a adapter. The adapter may be located in the housing and configured to guide the locking component.

In some embodiments, the safety fastener may have a first configuration in which the safety fastener is connected to the load lifting mechanism at the second fastener surface. The safety fastener in the first configuration may be immobile relative to the load lifting mechanism.

In some embodiments, the safety fastener may have a second configuration in which the safety fastener is disconnected from the load lifting mechanism and the working fastener is disengaged from the shaft assembly.

In some embodiments, the safety fastener in the second configuration may be immobile relative to the shaft assembly.

In some embodiments, the load lifting mechanism may include a first hole on the second fastener surface. The first hole may be a countersink. The safety assembly may include a locking component. The locking component may be in the countersink when the safety fastener is in the first configuration. The locking component may be out of the countersink when the safety fastener is in the second configuration.

In some embodiments, the at least a portion of the loading lifting mechanism and the working fastener form a one-piece component.

In some embodiments, the adapter may include a first contact surface and a second contact surface. The first contact surface may be connected to the limiting component at a top surface of the limiting component. The top surface may be a surface opposite to the second fastener surface and the second contact surface may be connected to the second fastener portion.

In some embodiments, the safety assembly may include a rotating component. The first contact surface may be connected to the limiting component through the rotating component at the top surface.

In some embodiments, the safety assembly may include an elastic component. The elastic component may be connected to the second fastener portion. The elastic component may be located between the adapter and a protruding portion of the locking component.

In some embodiments, the elastic component may be a spring.

In some embodiments, the driving device may include a motor and a gearbox, and the gearbox may be coupled to the shaft assembly.

Another aspect of the present disclosure relates to a lifting equipment. The lifting equipment may include a working assembly, a safety assembly and a shaft assembly. The working assembly may include a working fastener. The working fastener may be spirally connected to the shaft assembly. When the shaft assembly rotates the working fastener may move along the shaft assembly. The safety assembly may comprise a limiting component. The limiting component may be connected to the working fastener. A portion of the safety assembly may be in located a space between the limiting component and the working assembly.

In some embodiments, the safety assembly may include a safety fastener, and the safety fastener may be spirally connected to the shaft assembly.

In some embodiments, the safety assembly may include a rotating component, and the rotating component may be between the limiting component and the safety fastener.

In some embodiments, the safety assembly may have a first configuration and a second configuration. One of the working assembly or the safety assembly may have a first hole and the other has a locking component. The locking component may be in the first hole when the safety assembly is in the first configuration. The locking component may be out of the first hole when the safety assembly is the second configuration.

In some embodiments, the safety assembly may include an adapter and an elastic component. The adapter may be between the limiting component and the safety fastener. The elastic component may be between the adapter and the limiting component. The elastic force of the elastic component may be along the axis of the shaft assembly.

In some embodiments, the adapter may include a cavity. The safety fastener may include a through-hole. The safety fastener may be in the first configuration. A first end of the locking component may be in the cavity of the adapter and a second end of the locking component is in the through-hole of the safety fastener.

In some embodiments, the locking component may include a protrusion. The protrusion of the locking component may be between the first end of the locking component and the second end of the locking component.

In some embodiments, the protrusion of the locking component may be between the elastic component and the safety fastener.

In some embodiments, the lifting equipment may further include a load lifting mechanism. The load lifting mechanism may be configured to support a load and the working fastener may be connected to the limiting component through the load lifting mechanism.

Another aspect of the present disclosure relates to a C-arm medical device. The C-arm medical device may include a lifting device, a C-arm frame, a radiation source, a detector, and a carrier. The lifting device may include a working assembly, a safety assembly and a shaft assembly. The working assembly may include a working fastener. The working fastener may be spirally connected to the shaft assembly. When the shaft assembly rotates the working fastener may move along the shaft assembly. The safety assembly may comprise a limiting component. The limiting component may be connected to the working fastener. A portion of the safety assembly may be in located a space between the limiting component and the working assembly.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting examples, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by another expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Figure 1:
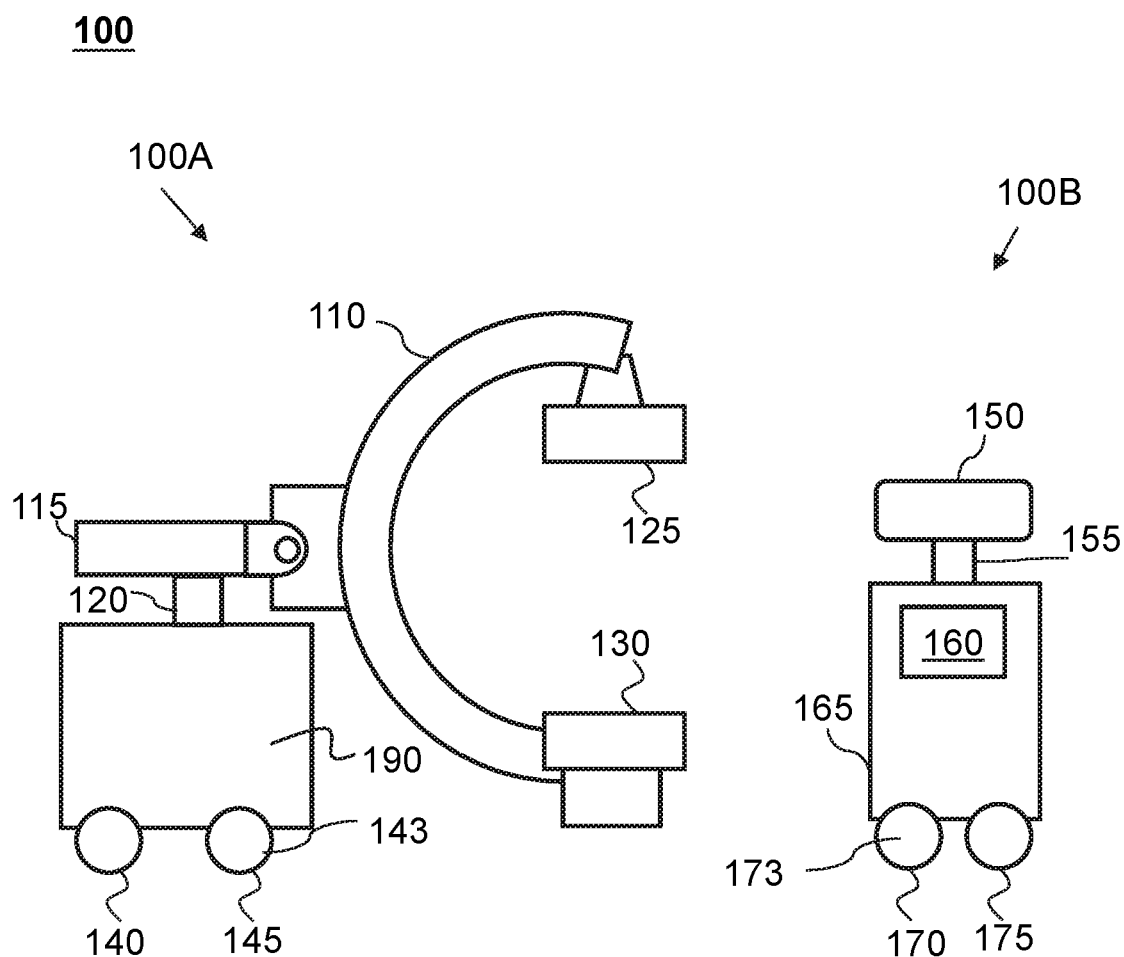
FIG. 1 is a schematic block diagram of an example of a medical imaging system according to some embodiments of the present disclosure.

FIG. 1 is a schematic block diagram of an exemplary medical imaging system 100 according to some embodiments of the present disclosure. The medical imaging system 100 may include a C-arm system 100A and a monitor trolley system 100B. It should be noted that the medical imaging system 100 described below is merely provided for illustration purposes, and not intended to limit the scope of the present disclosure. The imaging system may find its applications in various fields, such as healthcare equipment (e.g., medical applications), security applications, industrial applications, etc. For example, the medical imaging system 100 may be a digital radiography (DR) system, a multi-modality system, or the like, or a combination thereof. In some embodiments, the medical imaging system 100 may be used for internal inspections of an object including, e.g., flaw detection, security scanning, failure analysis, metrology, assembly analysis, void detection, wall thickness analysis, or the like, or a combination thereof. In some embodiments, the medical imaging system 100 may be a C-arm imaging system, a U-arm imaging system, a G-arm imaging system, or the like. The following descriptions are provided with reference to a C-arm imaging system as an example and this is not intended to limit the scope the present disclosure.

The C-arm system 100A may include a C-arm frame 110, a support arm 115, a lifting device 120, a detector 125, a radiation source 130, a first mobile assembly 143, a carrier 190, or the like.

The lifting device 120 may be configured to support the support arm 115. The lifting device 120 may be extendable to raise or lower the support arm 115. The lifting device 120 may include an anti-fall mechanism for the support arm 115. The support arm 115 may be configured to support the C-arm frame 110. The C-arm frame 110 may be configured to support the detector 125 and the radiation source 130. For example, the detector 125 and the radiation source 130 may be mounted on the C-arm frame 110 in an opposing arrangement. The first mobile assembly 143 may be configured to make the C-arm system 100A mobile. The first mobile assembly 143 may include one or more components including, for example, a first wheel 140, a second wheel 145, a third wheel (not shown in FIG. 1), a fourth wheel (not shown in FIG. 1), or the like. The one or more components may be the same or different in type, shape, size, and/or material. For example, a diameter of the first wheel 140 may be 10 cm and a diameter of the second wheel 145 may be 15 cm. The carrier 190 may be connected to the support arm 115. One or more components (e.g., a motor, a battery) may be mounted on the carrier 190. The mobile assembly 143 may be configured to support the carrier 190.

The radiation source 130 may emit electromagnetic radiation. The radiation may include a particle ray, a photon ray, or the like, or a combination thereof. The particle ray may include a beam of neutrons, a beam of protons (e.g., a α-ray), a beam of electrons (e.g., a β-ray), a beam of μ-mesons, a beam of heavy ions, or the like, or a combination thereof. The photon ray may include an X-ray, a γ-ray, ultraviolet, laser, or the like, or a combination thereof.

In some embodiments, an object may be placed between the detector 125 and the radiation source 130 for imaging. The object may include a substance, a tissue, an organ, a specimen, a body, a human being, or the like, or a combination thereof. By adjusting the position of the detector 125, the radiation source 130, and/or the object, the object may be positioned in a working area of the C-arm system 100A.

The detector 125 may detect radiation impinging on the detector 125. Some of the radiation may have traversed the object positioned in the working area of the C-arm system. The radiation may be emitted by the radiation source 130. The detector 125 may determine a signal based on the detected radiation. The attribute (e.g., a radiation amplitude) of the signal may correspond to a characteristic of the object. For example, a signal with a low radiation amplitude may represent that the radiation has traversed a tissue of high density (e.g., a bone tissue).

The detector 125 may include a scintillator layer that may absorb radiation, and emit visible light that can be detected by an array of photodiodes. The array of photodiodes may convert the visible light into an electrical signal. The radiation may be converted directly into an electrical signal by a suitable direct conversion material, such as amorphous selenium. The detector 125 may be and/or include a film-based detector. The scintillator layer may include a plurality of scintillators disposed in a plane in the form of a matrix. In some embodiments, the detector 125 may include a data acquisition circuitry that may sample the electrical signal received from the array of photodiodes via a plurality of signal transmission boards, and may convert the electrical signal to a digital signal for further processing.

It should be noted that, in some embodiments, an optoelectronic conversion unit (not shown in FIG. 1) may be external to the detector 125. The optoelectronic conversion unit may be an analog-digital converter (ADC). The analog-digital converter may convert the electronic signal into a digital signal, such as projected data indicative of the signal generated by the detector 125.

In some embodiments, the C-arm system 100A may be connected to a network (not shown in FIG. 1) for data communication. For instance, the C-arm system 100A may receive instructions, send out detected information, or the like, or a combination thereof, via, e.g., the network. The network may be a local area network (LAN), a wide area network (WAN), a public network, a private network, a proprietary network, a public switched telephone network (PSTN), the Internet, a virtual network, a metropolitan area network, a telephone network, or the like, or a combination thereof. The connection between different components in the C-arm system 100A may be wired or wireless. The wired connection may include using a metal cable, an optical cable, a hybrid cable, an interface, or the like, or a combination thereof. The wireless connection may include using a wireless local area network (WLAN), a wireless wide area network (WWAN), a Bluetooth, a ZigBee, a near field communication (NFC), or the like, or a combination thereof.

The monitor trolley system 100B may include a monitor 150, a monitor column 155, a processor 160, a monitor trolley 165, a second mobile assembly 173, or the like.

The monitor 150 may provide a user interface through which a user or an operator may communicate with different components in the C-arm system 100A. The monitor 150 may include a display (not shown in FIG. 1). The display may include a liquid crystal display (LCD), a light emitting diode (LED)-based display, or any other flat panel display, or may use a cathode ray tube (CRT), a touch screen, or the like. A touch screen may include, e.g., a resistance touch screen, a capacity touch screen, a plasma touch screen, a vector pressure sensing touch screen, an infrared touch screen, or the like, or a combination thereof. The monitor 150 may include an input device, a control panel, etc. The input device may include alphanumeric and other keys that may be input via a keyboard, a touch screen (for example, with a haptics or tactile feedback), a speech input, an eye tracking input, a brain monitoring system, or any other comparable input mechanism. The input device may also include, for example, a cursor control device, such as a mouse, a trackball, or cursor direction keys, etc.

The monitor 150 may display an image. The image may be generated by the medical imaging system 100. A user or an operator may provide a command or an instruction to the medical imaging system 100 via the monitor 150. For example, a user or an operator may provide, via the monitor device 150, a command to the lifting device 120 to make the lifting device 120 lift the C-arm frame 110 to a desired position. A user or operator may set, via the monitor 150, one or more parameters for the medical imaging system 100, including acquisition parameters and/or reconstruction parameters. The acquisition parameters may relate to one or more conditions in obtaining scan data by, for example, scanning an object. The reconstruction parameters may relate to one or more conditions in reconstructing an image of the object. For example, the acquisition parameters may include a tube voltage, a tube current, reconstruction parameters (e.g., a slice thickness), a scan time, a collimation/slice width, a beam filtration, a helical pitch, etc. The reconstruction parameters may include a reconstruction field of view (FOV), a reconstruction matrix, a convolution kernel/reconstruction filter, etc.

The monitor 150 may be supported by a monitor column 155. The monitor column 155 may be mounted on the monitor trolley 165. The second mobile assembly 173 (e.g., the third wheel 170 and the fourth wheel 175) may facilitate the moving of the monitor trolley 165.

The processor 160 may control the C-arm frame 110, the support arm 115, the lifting device 120, the detector 125, the radiation source 130, the first mobile assembly 143, the second mobile assembly 173, or the like. For example, the lifting device 120 may be controlled by the processor 160 to lift the C-arm frame 110 to a desired position that may be prescribed by a user. The processor 160 may control the parameters of radiation emission including, for example, the intensity of radiation beams. As another example, the processor 160 may control the display of images on the monitor 150. Furthermore, the processor 160 may control the data acquisition to acquire a signal generated from the radiation source 130. As still another example, the processor 160 may control the motion parameters of lifting device 120, including the distance to move, the velocity, and/or the direction.

The processor 160 may include a processor, a processing core, memory, or the like, or a combination thereof. Specifically, the processor 160 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a microcontroller unit, a microprocessor, an advanced RISC machines processor (ARM), or the like, or a combination thereof.

In some embodiments, the monitor trolley system 100B may be connected to a network (not shown in the figure) for data communication. For instance, the monitor trolley system 100B may receive instructions, provide position information, or the like, or a combination thereof, via, e.g., the network. The network may be a local area network (LAN), a wide area network (WAN), a public network, a private network, a proprietary network, a public switched telephone network (PSTN), the Internet, a virtual network, a metropolitan area network, a telephone network, or the like, or a combination thereof. The connection between different components in the monitor trolley system 100B may be wired or wireless. The wired connection may include using a metal cable, an optical cable, a hybrid cable, an interface, or the like, or a combination thereof. The wireless connection may include using a wireless local area network (WLAN), a wireless wide area network (WWAN), a Bluetooth, a ZigBee, a near field communication (NFC), or the like, or a combination thereof.

This description regarding the system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the lifting device 120 and the support arm 115 may be an integral piece. The lifting device 120 and the support arm 115 may be made of the same material. As a further example, there may be more or fewer wheels in the medical imaging system. As still another example, the monitor trolley system 110B may be integrated into the C-arm system 100A. However, those variations and modifications do not depart the scope of the present disclosure.

Figure 2:
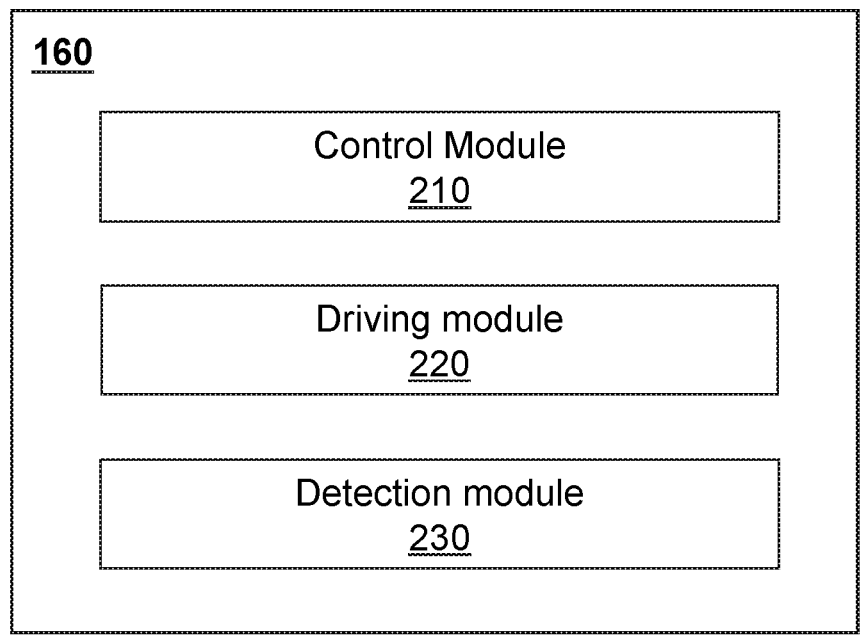
FIG. 2 illustrates an exemplary block diagram of the processor according to some embodiments of the present disclosure.

FIG. 2 illustrates an exemplary block diagram of the processor 160 according to some embodiments of the present disclosure. As shown in FIG. 2, the processor 160 may include a control module 210, a driving module 220, and a detection module 230. The different modules in the processor 160 may communicate with each other via a wireless connection or a wired connection, or a combination thereof. As an example, the wired connection may include an internal communication bus. As another example, the different modules may connect to and from a network to facilitate data communications via a communication (COM) port. The processor 160 may be part of the C-arm system 100A, or independent from but configured to communicate with the C-arm system 100A. For instance, the communication among the C-arm system 100A and the processor 160 may be achieved via a wired connection or a wireless connection, or a combination thereof.

The control module 210 may control the lifting device 120, the detector 125, the radiation source 130, the monitor 150, the driving module 220, and/or the detection module 230, or the like. The control module 210 may communicate with the driving module 220, and/or the detection module 230.

For illustration purposes, several examples are given below, but the examples do not limit the scope of the present disclosure. For example, the control module 210 may process data input by a user including, e.g., an imaging technician, or a doctor, via the monitor 150 and transform the data into specific commands, and supply the commands to the driving module 220. The monitor 150 may receive input and/or display output information. The input and/or output information may include programs, software, algorithms, data, text, number, images, voice, or the like, or any combination thereof. For example, a user or an operator may input some initial parameters or conditions to initiate a scan. As another example, some information may be imported from an external resource, such as a floppy disk, a hard disk, a wireless terminal, or the like, or any combination thereof. As still another example, the control module 210 may communicate with the other modules for exchanging information relating to the operation of the lifting device 120 or other parts of the C-arm system 100A. In some embodiments, the control module 210, the driving module 130, and/or the monitor 150 may be integrated into a console. Users may set parameters in C-arm lifting, control the lifting process, manage the abnormity through the console.

The driving module 220 may effectuate the movement of the shaft 345 via the power driving mechanism 480. For example, the driving module 220 may determine the output power of the power driving mechanism 480. As another example, the driving module 220 may determine when the power driving mechanism 480 starts to work and when the power driving mechanism 480 stops working. As still another example, the driving module 220 may determine the rotation direction of the gear in the power driving mechanism 480. The driving module 220 may control the direction and the angular velocity of the rotation of the shaft 345 via the power driving mechanism 480.

The driving module 220 may control the movement of the object via the power driving mechanism 480. For example, the moving velocity of the object may be controlled by the driving module 220 based on the amplitude of the output power of the power driving mechanism 480. As another example, the height to be moved may be controlled by the driving module 220 based on the amplitude and duration of the output power supply of the power driving mechanism 480. As still another example, the moving direction of the object may be controlled by the driving module 220 based on the rotation direction of the gear in the power driving mechanism 480.

The detection module 230 may detect an abnormity of the lifting device 120. The detection module 230 may generate a warning message. The warning message may be displayed on the monitor 150 when an abnormity is detected. The detection module 230 may send a message to the control module 210 automatically when an abnormity is detected. The message may trigger the control module 210 to stop the shaft 345 from rotating.

For illustration purposes, several examples are given below. It is understood that the examples do not limit the scope of the present disclosure. For example with reference to FIG. 4, components of a distance detector assembly may be disposed on the working fastener 490 and the safety fastener 470, respectively. The distance detector assembly may be configured to detect the distance between the working fastener 490 and the safety fastener 470. The detection module 230 may monitor the distance between the working fastener 490 and the safety fastener 470 via the distance detector assembly. The detection module 230 may detect the abnormity of the lifting device 120 when the distance between the working fastener 490 and the safety fastener 470 changes. As another example also with reference to FIG. 4, a height monitor may be disposed on the load lifting mechanism 404. The height monitor may monitor the height of the load lifting mechanism 404. The detection module 230 may detect the abnormity of the lifting device 120 when the height of the load lifting mechanism 404 stays unchanged and the power driving mechanism 480 is working. As still another example, a photogate may be placed inside the countersink 460. The photogate may include a light source and a receiver. The light source may emit light. The light emitted by the light source may be detected by the receiver. The light emitted by the light source may be blocked by the locking component 450. The detection module 230 may detect the abnormity of the lifting device 120 when the receiver receives light emitted from the light source.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the detection module 230 may be omitted. However, those variations and modifications do not depart the scope of the present disclosure.

Figure 3:
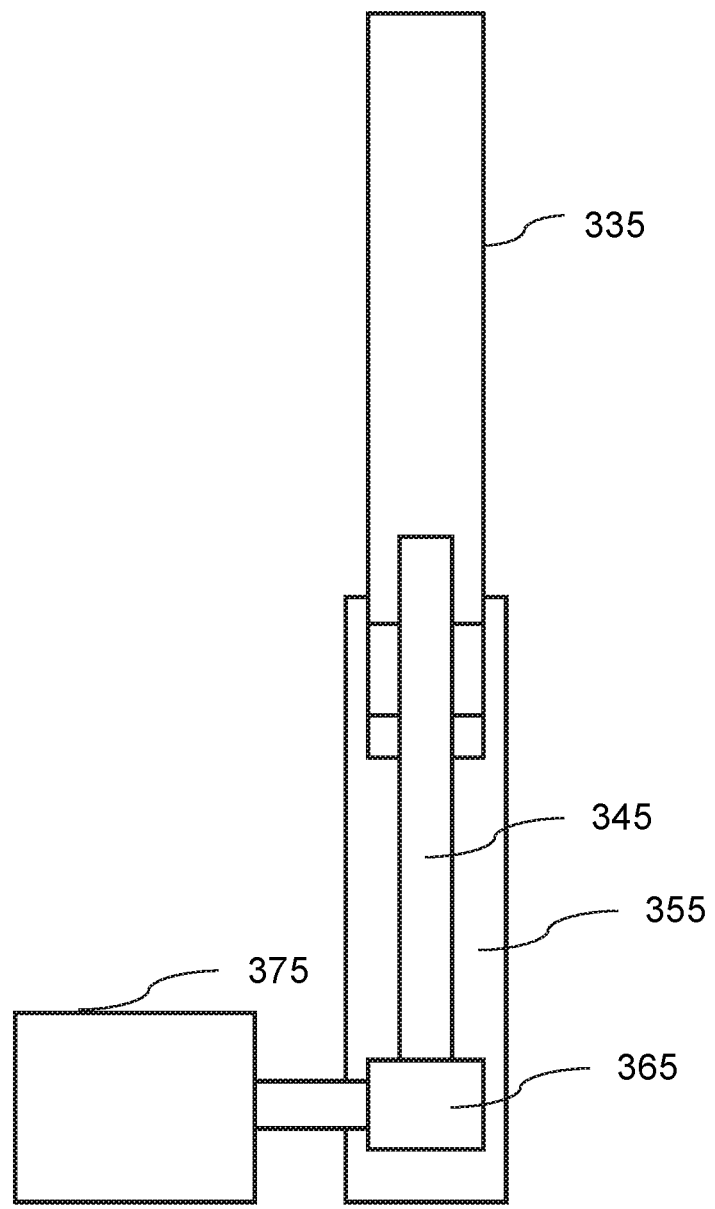
FIG. 3 illustrates a cross-sectional view of an exemplary lifting device according to some embodiments of the present disclosure.

FIG. 3 illustrates a cross-sectional view of an exemplary lifting device 120 according to some embodiments of the present disclosure. As shown, the lifting device 120 may include a shaft 345. The lifting device 120 may operably connect to an object 335 loaded on the lifting device 120, an immobilization mechanism 355, a gearbox 365, and a driving device 375, or the like.

The object 335 may be located at the top of the lifting device 120. In some embodiments, the object 335 may be the support arm 115. The object 335 may be loaded on the lifting device 120 through the load lifting mechanism 404. The loaded object 335 may vertically move from a first height to a second height. The movement may be supported by the load lifting mechanism 404.

The shaft 345 may be located in the middle of the lifting device 120. The shaft 345 may be a screw thread rod or a ball screw rod. The shaft 345 may be coupled to the driving device 375. The driving device 375 may be coupled to the bottom part of the shaft 345 through the gearbox 365. The shaft 345 may be threadedly engaged with a working fastener 490 and/or a safety fastener 470.

The shaft 345 may be configured to drive the working fastener 490 to move along the shaft 345. Merely by way of example, the working fastener 490 may move from a first height to a second height when the shaft 345 rotates under the force supplied by the driving force 375. In some embodiments, the safety fastener 470 may move simultaneously with the working fastener 490 along the shaft 345.

Figure 4:
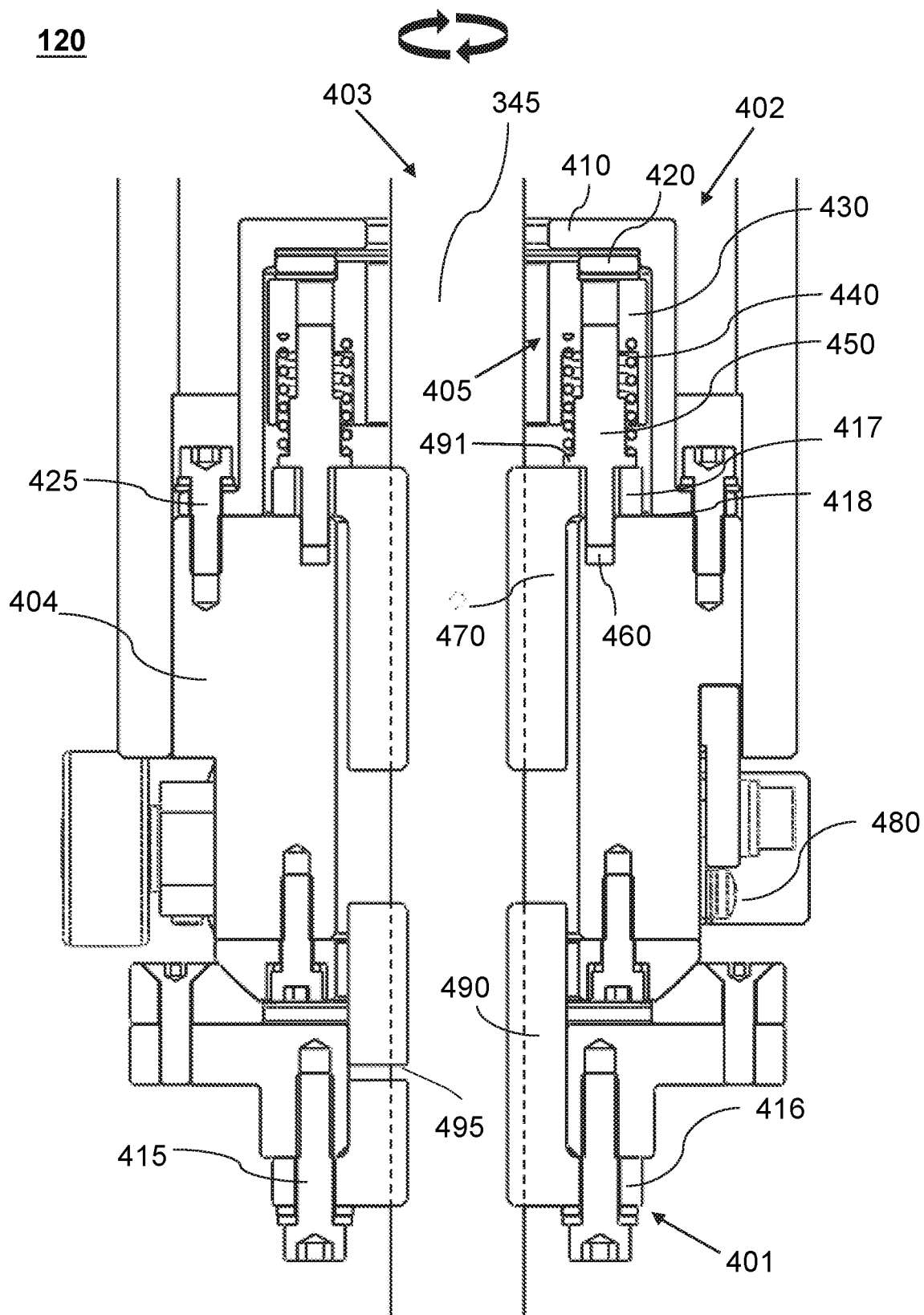
FIG. 4 illustrates a cross-sectional view of an exemplary lifting device according to some embodiments of the present disclosure.

In some embodiments, the shaft 345 may be a ball screw shaft. The ball screw shaft may be disposed end to end with an output shaft of the driving device 375. The driving device 375 may include a proportional type DC motor. The proportional type DC motor may be controlled by the control module 210 and/or the driving module 220. The physical connection between the ball screw shaft and the output shaft of the driving device 375 may be based on a coupling member. The coupling member may transmit a rotational driving force from the driving device 375 to the ball screw shaft. The coupling member may be a gearbox 365. The ball screw shaft and the output shaft of the driving device 375 may be aligned with each other so that their axes substantially coincide. In some embodiments, the shaft 345 may be a ball screw shaft, the safety fastener 470 and the working fastener 490 may be a ball nut as illustrated in FIG. 4. The ball screw shaft 345 may include a ball circulating groove that extends over the outside surface of ball screw shaft 345. The ball circulating groove may accommodate and allow the movement of a ball of the ball nut. The ball circulating groove may be in the form of helical threads.

The ball nut may serve as a movable nut screwed on the ball screw shaft. The ball nut may be configured to move axially in accordance with the rotation of the ball screw shaft. The ball nut may be configured to remain immobile in the vertical direction when the driving device 375 is working. The ball nut may fall when without the support of the driving device 375 stops working.

In some embodiments, the shaft 345 may be a screw shaft, the safety fastener 470 and/or the working fastener 490 may be a screw nut. The screw nut may be formed with an internal thread configured to engage with the external helical threads of the threaded screw shaft.

The screw nut may include a self-locking mechanism. The screw nut may remain immobile in the vertical direction when the driving device 375 stops working. The screw nut may be configured to translate the rotation of the threaded screw shaft into a linear motion of the screw nut and produce an axial force. The screw nut may be configured to rotate with the threaded screw shaft and remain immobile in the vertical direction. For example, the first screw nut may be configured to remain immobile in the vertical direction when the working fastener 490 is disengaged with the shaft 345.

In some embodiments, the shaft 345 may be a threaded screw shaft. The threaded screw shaft may include external helical threads extending over the outside surface of the shaft 345. The connection between the threaded screw shaft and the driving device 375 may be the same as the connection between the ball screw shaft and the driving device 375. The working fastener 490 and the safety fastener 470 may be screw nuts when the shaft 345 is a threaded screw shaft.

The immobilization mechanism 355 may be configured to immobilize the shaft 345. The end of the shaft that is coupled to the immobilization mechanism 355 may rotate relatively to the immobilization mechanism 355.

The driving device 375 may be located at the bottom of the lifting device 120. The driving device 375 may include one or more motors. The one or more motors may be mounted within a chamber on one side of the lifting device 120. In some embodiments, the one or more motors may be secured to at least one sidewall and/or the floor of the chamber to prevent or reduce undesired vibrations or rotation. The one or more motors may be a direct current bi-directional motor. The one or more motors may be a reversible DC motor. Electrical power and direction control for the one or more motors may be provided by the processor 160.

In some embodiments, the driving device 375 may be connected to the shaft 345 via the gearbox 365 and the output shaft of the driving device 375. A clutch may be connected to the output shaft. The clutch may provide a selective engagement between the output shaft and the gearbox 365. The clutch may be an electromechanical tooth clutch. The clutch may be configured to engage the gearbox 365 when the driving device 375 is activated. When the clutch is engaged, torque may be transferred from the driving device 375 to the gearbox 365. When the clutch 44 is disengaged, torque may not be transferred from the driving device 375 to the gearbox 365.

The gearbox 365 may be located at the bottom of the lifting device 120. The gearbox 365 may contain a gear reducer. The gear reducer may include gearbox bearings, shafts, gears, pulleys, a belt, sprockets, a chain, or the like, or a combination thereof. The gear reducer of the gearbox 365 may have an input mechanically coupled to the output shaft of the driving device 375. The gear reducer of the gearbox 365 may have an output mechanically coupled to the shaft 345. The shaft 345 may be driven to rotate in response to a rotation of the output shaft via the gear reducer.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the clutch may be omitted. However, those variations and modifications do not depart the scope of the present disclosure.

FIG. 4 illustrates a cross-sectional view of an exemplary lifting device 120 according to some embodiments of the present disclosure. As shown, the lifting device may include a working assembly 401, a safety assembly 402, a shaft assembly 403, a load lifting mechanism 404, and a power driving mechanism 480, or the like. The safety assembly 402 and the shaft assembly 403 may constitute an anti-fall mechanism for lifting equipment. The anti-fall mechanism may be configured to support the load lifting mechanism 404 such that when a working fastener 490 of the working assembly 401 fails the loading mechanism 404 does not drop. Dashed lines may represent some portions (e.g., edges) of the lifting device 120 invisible or hidden from the view of FIG. 4.

The working assembly 401 may be configured to support a subject. The subject may be the load lifting mechanism 404. The working assembly 401 may be coupled to the load lifting mechanism 404. As used herein, "object A couple to object B" means a force may be transfer from A (e.g., the working assembly 401) to B (e.g., the load lifting mechanism 404). In some embodiments, the load lifting mechanism 404 may be a lifting pulley. The working assembly 401 may be coupled to the shaft assembly 403. For example, the working fastener 490 may be spirally connected to the shaft assembly 403. The physical connection between the working assembly 401 and the load lifting mechanism 404 may be realized by a second screw 415.

The working assembly 401 may include a working fastener 490, a first protruding portion 416, a second screw 415, or the like, or a combination thereof. The working fastener 490 may contact the shaft 345. The working fastener 490 may move along the shaft 345. The second screw 415 may be configured to connect the working fastener 490 and the load lifting mechanism 404.

The working fastener 490 may connect to the shaft assembly 403. The working fastener 490 may move from a first height (e.g., a middle position along the shaft assembly 403) to a second height (e.g., the top of the shaft assembly 403) along the shaft assembly 403.

The working fastener 490 may be a nut. The nut may be a ball nut, a trapezoidal screw thread nut, an acme nut, a square nut, a swage nut, or the like. The ball nut may be of an external ball return system, an internal ball return system, or the like. The ball nut may be a return-pipe nut, a simple nut, a large-lead nut, or the like. The return-pipe nut may use a return pipe for ball circulation. The return pipe may allow balls to be picked up, pass through the pipe, and return to their original positions to carry out continuous motion. Balls in the simple nut may change their traveling direction with a deflector, pass over the circumference of the screw shaft, and return to their original positions to carry out continuous motion. Balls in the large-lead nut may be picked up with an end cap, pass through the through hole of the nut, and return to their original positions to carry out continuous motion. The acme nut may be a standard nut, an anti-backlash nut, or the like.

The working fastener 490 may be made of any material, such as a metal (e.g., steel, cuprum, bronze, etc.), an alloy, a non-metallic material (e.g., plastic, carbon, etc.), a composite material (e.g., polymer, etc.), a rigid material, an elastic material, or the like, or a combination thereof.

The working fastener 490 may include a hole 495. The hole may be an oil filler hole. The hole may be configured such that lubrication oil may be added to the lifting device 120. An angle between the central line of the hole 495 and the horizontal plane may be any value (e.g., 0°, 15°, 43°, 72°, 94°, 120°, and 180°, etc). The inner cross section of the hole 495 may be of any shape, for example, the shape of a rectangle, a circle, a triangle, a polygon, etc.

The working fastener 490 may include a hollow cylinder and a head. The diameter of the hollow cylinder and the diameter of the head may be the same or different. For example, the head may have a larger diameter than the hollow cylinder. An internal screw thread may be formed on the inner surface of the hollow cylinder. The internal screw thread may be complementary to an external screw thread of the shaft 345. The screw thread (e.g., the internal screw thread of the working fastener 490, or the external screw thread of the shaft 345) may be a ball screw thread, or a trapezoidal screw thread, or the like. In some embodiments, a first connecting portion of the working fastener 490 may refer to the portion of the hollow cylinder that mechanically connects the working fastener 490 to the shaft 345. The inner diameter of the hollow cylinder may be slightly larger than a diameter of the shaft 345. As used herein, "slightly" indicates that the difference between two parameters (e.g., diameter, radius, circumference, area, etc.) is less than 25%, or less than 20%, or less than 15%, or less than 10%, or less than 8%, or less than 5%, etc., of the larger of the two parameters. The space between the hollow cylinder of the working fastener 490 and the shaft 345 may be filled with a gas (e.g., air), a lubricant, etc. The head of the working fastener 490 may protrude in the horizontal direction to generate the first protruding portion 416. The head may have a hole in the first protruding portion 416. The second screw 415 may be inserted into the hole. In some embodiments, a first fastener portion of the working fastener 490 may be the first protruding portion 416 that connects the working fastener 490 to the load lifting mechanism 404 via the second screw 415.

The second screw 415 may be configured to assemble the working fastener 490 and the load lifting mechanism 404. The second screw 415 may be a drywall screw, a lag screw, a sheet metal screw, a twinfast screw, or the like, or a combination thereof. The second screw 415 may be made of any material, an alloy (e.g., aluminum alloy), a polymer-based composite material, etc.

In some embodiments, the second screw 415 may have helical threads extending over the surface. The helical threads may be configured to engage with the working fastener 490 and the load lifting mechanism 404. For example, the working fastener 490 may have a hole with internal threads. The internal threads of the working fastener 490 may be complementary to the helical threads of the second screw 415. The load lifting mechanism 404 may have a hole with internal threads. The internal threads of the load lifting mechanism 404 may be complementary to the helical threads of the second screw 415. The hole of the working fastener 490 and the hole of the load lifting mechanism 404 may be aligned to accommodate the second screw 415. The working fastener 490 and the load lifting mechanism 404 may be assembled together when the second screw 415 is inserted into the hole of the working fastener 490 and the hole of the load lifting mechanism 404.

In some embodiments, the second screw 415 may be omitted. For example, the working fastener 490 may be coupled to the load lifting mechanism 404 by bonding, welding, etc. The bonding may be formed by connecting the working fastener 490 with the load lifting mechanism 404 using an adhesive material. The adhesive material may include, e.g., resin (e.g., epoxy resin, phenolic resin, polyurethane, polystyrene, polyacrylate, ethylene-vinyl acetate copolymer, vinyl acetate resin, and acrylic resin, etc.), rubber (e.g., butyl rubber, chlorinated rubber, and nitrile rubber, etc.), or the like, or a combination thereof. The welding may connect multiple components by a welding material, such as a thermoplastic material (e.g., resin, rubber).

In some embodiments, the working fastener 490 and the lifting mechanism 404 may be assembled together. In some embodiments, one or more coupling structures (e.g., one or more rivets, screws, bolts, pins joints, key joints) may be arranged between the working fastener 490 and the lifting mechanism 404 to assemble them together.

The safety assembly 402 may be configured to prevent the load lifting mechanism 404 from dropping when the working assembly 401 fails. As used herein, that the working assembly 401 fails means the working assembly 401 is unable to support the load lifting mechanism 404. For example, the working assembly 401 may fail when the working fastener is disengaged from the shaft 345. The safety assembly 402 may be coupled to the load lifting mechanism 404. The safety assembly 402 may be coupled to the shaft assembly 403. For example, the safety fastener 470 may be spirally connected to the shaft assembly 403. The safety assembly 402 (e.g., the safety fastener 470) may move along the shaft 345.

The safety assembly 402 may include a limiting component 410, a rotating component 420, an adapter 430, an elastic component 440, a locking component 450, a countersink 460, a safety fastener 470, a housing 405, a first screw 425, a second protruding portion 417, or the like, or a combination thereof.

In some embodiments, the safety assembly 402 may be connected to the load lifting mechanism 404 based on the first screw 425. The safety assembly 402 may be connected to the load lifting mechanism 404 based on the locking component 450. The locking component 450 may include a protruding portion 491 (or referred to as a protrusion for brevity). A cross section of the protrusion of the locking component 450 may be of any shape (e.g., rectangle, circle, triangle, a polygon, etc.). The locking component 450 may have a first end and a second end, and the protrusion of the locking component 450 may be between the first end and the second end. The first end of the locking component 450 may be connected to the safety assembly 402. The second end of the locking component 450 may be connected to the load lifting mechanism 404. In some embodiments, the safety assembly 402 may be connected to the working assembly 401 based on the locking component 450. For example, the first end of the locking component 450 may be connected to the safety fastener 470 and the second end of the locking component 450 may be connected to the working fastener 490.

The safety fastener 470 may be configured to support the load lifting mechanism 404. For example, the safety fastener 470 may support the load lifting mechanism 404 when the working fastener 490 fails. The safety fastener 470 and the working fastener 490 may be of the same type or different types. In some embodiments, the safety fastener 470 and/or the working fastener 490 may be a self-locking fastener. For example, the safety fastener 470 and/or the working fastener 490 may be a screw nut with a self-locking mechanism. As another example, the safety fastener 470 and/or the working fastener 490 may be a ball nut without a self-locking mechanism.

The safety fastener 470 may include a hollow cylinder and a head. The diameter of the hollow cylinder and the diameter of the head may be the same or different. For example, the head may have a larger diameter than the diameter of the hollow cylinder. An internal screw thread may be formed on the inner surface of the hollow cylinder. The internal screw thread may be complementary to an external screw thread of the shaft 345. The screw thread (e.g., the internal screw thread of the safety fastener 470, or the external screw thread of the shaft 345) may be a ball screw thread, or a trapezoidal screw thread, or the like. In some embodiments, a second connecting portion of the safety fastener 470 may refer to the portion of the hollow cylinder that mechanically connects the safety fastener 470 to the shaft 345. The inner diameter of the hollow cylinder of the safety fastener 470 may be slightly larger than the diameter of the shaft 345. The space between the hollow cylinder of the safety fastener 470 and the shaft 345 may be filled with a gas (e.g., air), a lubricant, etc. The head of the safety fastener 470 may protrude in the horizontal direction to generate the second protruding portion 417. The head may have a hole (e.g., a through-hole) in the second protruding portion 417. The safety fastener 470 and the load lifting mechanism 404 may be connected to each other using the locking component 450. For instance, the locking component 450 may be inserted into the hole in the second protruding portion 417 and the countersink 460. A second fastener portion of the safety fastener 470 may be the second protruding portion 417 that connects the safety fastener 470 to the load lifting mechanism 404 via the locking component 450.

A distance between the safety fastener 470 and the working fastener 490 may be fixed or variable. In some embodiments, the safety fastener 470 may be stationary in a vertical direction of the shaft 345. The working fastener 490 may move from a first vertical position to a second vertical position of the shaft 345. The distance between the safety fastener 470 and the working fastener 490 may change with the movement of the working fastener 490. In some embodiments, the safety fastener 470 and the working fastener 490 may move in a synchronized manner such that the distance between the safety fastener 470 and the working fastener 490 may be fixed. The safety fastener 470 may move by the same distance and/or at the same rate as the working fastener 490.

The safety fastener 470 may have a first configuration and a second configuration. In the first configuration, the second protruding portion 417 of the safety fastener 470 is connected to the load lifting mechanism 404 at a second fastener surface 418 as described in connection with the housing 405 in FIG. 4. The locking components 450 may be placed in the second protruding portion 417 of the safety fastener 470 and the countersink 460 under an elastic force from the elastic component 440 in the vertical direction. The safety fastener 470 may be immobile relative to the load lifting mechanism 404. The circumferential movement of the safety fastener 470 may be confined by the locking component 450. For example, the safety fastener 470 may not rotate with the shaft 345 when the shaft 345 rotates under the driving force supplied by a driving device 375. The working fastener 490 may support the load lifting mechanism 404. The safety fastener 470 does not function as a load-bearing fastener to bear a weight from the load lifting mechanism 404. In the first configuration, the wear and tear of the safety fastener 470 may be limited and slight. The load-bearing fastener of the lifting device 120 may be the working fastener 490. The wear and tear of the working fastener 490 may be serious. The wear and tear of the safety fastener 470 may be smaller than that of the working fastener 490.

In the second configuration, the safety fastener 470 may be apart from the load lifting mechanism 404 at the second protruding portion 417. The working fastener 490 does not support the load lifting mechanism 404. The safety fastener 470 may serve as a load-bearing fastener. For example, the working fastener 490 may be disengaged from the shaft 345 when the working fastener 490 fails due to, for example, overload, a defect of the working fastener 490, or the like, or a combination thereof. Without the safety assembly 402, the load lifting mechanism 404 may fall when the disengagement occurs.

In the second configuration, the working fastener 490 may no longer support the load lifting mechanism 404. The rotation of the shaft 345 may drive the safety fastener 470 to move in the upward direction. Here, the term "upward direction" is the direction pointing from the working fastener 490 to the safety fastener 470. The limiting component 410 may bear the loading of the falling load lifting mechanism 404 due to the connection between the limiting component 410 and the load lifting mechanism 404. The connection may be established by inserting the first screw 425 into a hole of the load lifting mechanism 404. The limiting component 410 may fall due to the loading. The safety fastener 470 may rotate linearly in the axial direction of the shaft 345 at the same time. On the one hand, the locking component 450 may be pushed by the safety fastener 470 to move in the upward direction. On the other hand, the locking component 450 may be pushed by the elastic force of the elastic component 440 to move in the downward direction. The pushing force from the safety fastener 470 may be greater than the elastic force of the elastic component 440. The locking component 450 may move in the upward direction and out of the countersink 460. The safety fastener 470 may bear the loading of the load lifting mechanism 404 via the limiting component 410, the locking component 450, and the rotating component 420. The load lifting mechanism 404 may connect to the limiting component 410 via the first screw 425. In this way, the safety fastener 470 may prevent the load lifting mechanism 404 from dropping when the working fastener 490 is disengaged from the shaft 345.

In the second configuration, the locking component 450 may move in the upward direction until the locking component 450 is out of the countersink 460. The restriction on the circumferential movement of the safety fastener 470 may be released when the locking component 450 is out of the countersink 460.

In some embodiments, the safety fastener 470 may rotate with the shaft 345 when the shaft 345 rotates under the driving force supplied by a driving device 375. The resistance the safety fastener 470 is subject to may be small when it rotates with the shaft 345 as the safety fastener 470 is connected to the rotating component 420. The safety fastener 470 may remain immobile in the vertical direction when it rotates with the shaft 345. The load lifting mechanism 404 may remain immobile in the vertical direction as it is supported by the safety fastener 470. The static status of the load lifting mechanism 404 may indicate an abnormality.

The limiting component 410 may be located at the top of the lifting device 120. The limiting component 410 may have any suitable shape and/or dimension. The cross-section of the limiting component 410 may have the shape of a rectangle, a trapezoid, a circle, an ellipse, a polygon, or any irregular shape. For example, the cross-section of the limiting component 410 may have a shape of a capital Z as illustrated in FIG. 4. The bottom part of the capital Z may be a base with a cross-section having a shape of a rectangle. The top part of the capital Z may be configured to contact the rotating component 420. The limiting component 410 may be made of any material, such as a material with high tensile strength (e.g., a polymer-based composite material), a material with high yield strength, and an alloy, or the like.

The projection of the limiting component 410 may partially overlap with the projection of the safety fastener 470 in a plane perpendicular to the shaft assembly 403 (e.g., the horizontal plane when the shaft assembly 403 is set in a vertical direction).

In some embodiments, the load lifting mechanism 404 and the limiting component 410 may be manufactured together as a one-piece component. In some embodiments, the limiting component 410 and the load lifting mechanism 404 may be different components. The limiting component 410 may connect to the load lifting mechanism 404 through one or more screws (e.g., the first screw 425), bonding, and welding, or any other suitable manners. In some embodiments, the one or more screws may be a drywall screw, a lag screw, a sheet metal screw, a twinfast screw, or the like, or a combination thereof.

A housing 405 may be located between the limiting component 410 and the load lifting mechanism 404. In some embodiments, the second fastener surface 418 of the lifting mechanism 404 may be in contact with the safety fastener 470 and the limiting component 410. The housing 405 may be located between the limiting component 410 and the second fastener surface 418 of the lifting mechanism 404. The second fastener portion of the safety fastener 470 may be located in the housing 405.

In some embodiments, the second fastener portion may accommodate the rotating component 420, the adapter 430 and, the elastic component 440. The rotating component 420 may be located below the limiting component 410. The adapter 430 may be located below the rotating component 420. The elastic component 440 may be disposed between the adapter 430 and the locking component 450. The locking component 450 may be in the countersink 460 when the working fastener 490 works as a load-bearing fastener. The locking component 450 may be out of the countersink 460 when the safety fastener 470 working as a load-bearing fastener.

The rotating component 420 may be configured to decrease a rotational resistance. The rotating component 420 may be disposed between the safety fastener 470 and the limiting component 410. For example, the rotation resistance may be generated when the safety fastener 470 rotates with the shaft 345. The rotational resistance may be generated between the top part of the limiting component 410 and a first contact surface of the adapter 430. The first contact surface may be in the top part of the adapter 430. The first contact surface may face the rotating component 420. In some embodiments, the rotating component 420 may be an end bearing.

The rotating component 420 may be made of any material, such as a material with high abrasive resistance (e.g., a polymer-based composite material, an alloy, etc.). The rotating component 420 may have any suitable shape and/or dimensions. For example, the cross-section of the rotating component 420 may have the shape of a rectangle, a circle, an ellipse, a polygon, or any irregular shape.

The adapter 430 may be configured to support the limiting component 410. The support may be provided by the safety fastener 470. The adapter 430 may also be configured to guide the locking component 450. For example, the locking component 450 may rotate along a predetermined track under the constraint of the adapter 430.

In some embodiments, the adapter 430 may have any suitable shape and/or dimensions. The adapter 430 may form a cavity. The cavity may be inside the housing 405. The cavity may be semi-open. The cavity may be configured to accommodate the locking component 450 and/or the elastic component 440.

The elastic component 440 may be configured to protect the safety assembly 402. The elastic component 440 may be connected to the second fastener portion. The elastic component 440 may be located between the second fastener portion of the safety fastener 470 and the limiting component 410. The elastic component 440 may be a coil spring. The elastic component 440 may be filled with compressed gas.

In some embodiments, the elastic deformation of the elastic component 440 may be along an axis that substantially coincides with the axis of the shaft 345. The elastic component 440 may be configured to push the top side of the rotating component 420 to contact the limiting component 410.

In some embodiments, the elastic component 440 may be configured to push the locking component 450 to traverse a hole in the safety fastener 470 and to be housed in the countersink 460. The circumferential movement of the safety fastener 470 may be confined when the locking component 450 is in the countersink 460. In that circumstance, the safety fastener 470 may not rotate with the shaft 345 and may remain stationary relatively to the load lifting mechanism 404 when the shaft 345 rotates.

In some embodiments, the elastic component 440 may provide a portion of a cushioning force to the safety assembly 402 when the working fastener 490 is disengaged from the shaft assembly 403. The elastic component 440 may be configured to reduce the impact force exerted by the load lifting mechanism 404 on the safety fastener 470. The elastic component 440 may be configured to reduce the probability that the safety fastener 470 is damaged when the working fastener 490 is disengaged from the shaft assembly 403.

In some embodiments, the load lifting mechanism 404 and the working fastener 490 may be manufactured together as a one-piece component.

The shaft assembly 403 may be configured to cause the working fastener 490 and/or the safety fastener 470 to move. The shaft assembly 403 may be connected to the power driving mechanism 480. The shaft assembly 403 may include a shaft 345. The shaft 345 may be located in the center portion of the lifting device 120.

The load lifting mechanism 404 may be configured to bear the load of an object. The object may be the loaded object 335 illustrated in FIG. 3. The object may be the C-arm 110 in connection with FIG. 1A. The load lifting mechanism 404 may be located at two opposite sides of the lifting device 120. A portion of the load lifting mechanism 404 may be between the working assembly 401 and the safety assembly 402.

The load lifting mechanism 404 may have any suitable shape and/or dimensions. For example, the cross-section of the load lifting mechanism 404 may have the shape of a rectangle, a trapezoid, a circle, an ellipse, a polygon, or any irregular shape. For example, the cross-section of the load lifting mechanism 404 may have the shape of an inverted L as illustrated in FIG. 4.

The load lifting mechanism 404 may have one or more holes, such as a countersink 460, a hole on a first fastener surface connected to the limiting component 410, and a hole on the second fastener surface 418 connected to the working fastener 490, etc. The countersink 460 may be configured to connect the locking component 450. The countersink 460 may be deep enough to allow a horizontal surface of the locking component 450 to contact the top surface of the safety fastener 470 as illustrated in FIG. 4. The term "horizontal surface" is a surface substantially parallel to the second fastener surface 418. The safety fastener 470 does not rotate with the shaft 345 when the locking component 450 is inside the countersink 460. The safety fastener 470 may rotate with the shaft 345 when the locking component 450 is outside of the countersink 460. There may be an abnormity when the locking component 450 is outside of the countersink 460. The abnormity may indicate that the working assembly 401 does not function properly.

In some embodiments, the load lifting mechanism 404 may be configured to move an object (e.g., the loaded object 335) from a first position to a second position (e.g., from a first height to a second height). In some embodiments, the load lifting mechanism 404 may be supported by the working fastener 490 via the second screw 415 and to remain immobile relative to the working fastener 490 when the working fastener 490 is engaged with the shaft 345. In some embodiments, the load lifting mechanism 404 may fall when the working fastener 490 is disengaged from the shaft 345 and the locking component 450 has not yet been coupled to the rotating component 420. In some embodiments, the load lifting mechanism 404 may be secured by the safety fastener 470 via the first screw 425 and to remain immobile relative to the safety fastener 470 when the working fastener 490 is disengaged from the shaft 345. For example, the load lifting mechanism 404 may be secured by the safety fastener 470 when the locking component 450 is coupled to the rotating component 420.

The power driving mechanism 480 may be configured to provide a driving force for the lifting device 120. The power driving mechanism 480 may be located on one side of the lifting device 120. The power driving mechanism 480 may be mounted on the load lifting mechanism 404.

The power driving mechanism 480 may include, for example, a motor, a reduction gear, or the like, or a combination thereof. In some embodiments, the power driving mechanism 480 may include a driving device 375 and a gearbox 365 as illustrated in FIG. 3.

The power driving mechanism 480 may be configured to provide a driving force for the shaft 345. For example, the power driving mechanism 480 may be configured to rotate the shaft 345. The power driving mechanism 480 may be configured to rotate the shaft 345 in one or more directions (e.g., clockwise, anti-clockwise). The power driving mechanism 480 may be configured to rotate the shaft 345 at a certain angular velocity. An object may be moved from a first height to a second height when the power driving mechanism 480 rotates the shaft 345. The power driving mechanism 480 may be controlled by the driving module 220. For example, the output power of the power driving mechanism 480 may be determined by the driving module 220. The intensity and time span of the output power of the power driving mechanism 480 may be determined by the driving module 220. As another example, the rotation direction of the gear in the power driving mechanism 480 may be determined by the driving module 220. The direction and the angular velocity of the rotation of the shaft 345 may depend at least partially on the operation of the power driving mechanism 480.

The power driving mechanism 480 may control the movement of the object. For example, the power driving mechanism 480 may control the moving velocity of the object based on the amplitude of the output power of the power driving mechanism 480. As another example, the power driving mechanism 480 may control the height to be moved based on the amplitude and/or duration of the output power of the power driving mechanism 480. As still another example, the power driving mechanism 480 may control the moving direction of the object based on the rotation direction of the gear in the power driving mechanism 480.

In some embodiments, an output shaft of the power driving mechanism 480 may be coupled to the end portion of the shaft 345, and may rotate the shaft 345. In some embodiments, the working fastener 490 may be engaged with the shaft 345, and the circumferential movement of the working fastener 490 may be confined by the second screw 415. Therefore, when the power driving mechanism 480 rotates the shaft 345, the working fastener 490 may move upward or downward corresponding to a rotation direction of the shaft 345. In some embodiments, the safety fastener 470 may be engaged with the shaft 345, and the circumferential movement of the working fastener 470 may be confined by the locking component 450. Therefore, when the power driving mechanism 480 rotates the shaft 345, the safety fastener 470 may move upward or downward based on a rotation direction of the shaft 345. In some embodiments, the safety fastener 470 may be engaged with the shaft 345, and the constraint on the circumferential movement of the safety fastener 470 may be removed when the locking component 450 is out of the countersink 460. Therefore, when the power driving mechanism 480 rotates the shaft 345, the safety fastener 470 may rotate with the shaft 345 and remain immobile in the vertical direction.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the physical connection between the working fastener 490 and the load lifting mechanism 404 and/or physical connection between the limiting component 410 and the load lifting mechanism 404 may be achieved using different techniques. For example, the working fastener 490 may be coupled to the load lifting mechanism 404 by bonding using an adhesive material, while the limiting component 410 may be coupled to the load lifting mechanism 404 by welding using a welding material. The safety fastener 470 may include an oil filler hole. In some embodiments, the oil filler hole may be configured such that lubrication oil may be added to the lifting device 120. However, those variations and modifications do not depart the scope of the present disclosure.

Figure 5:
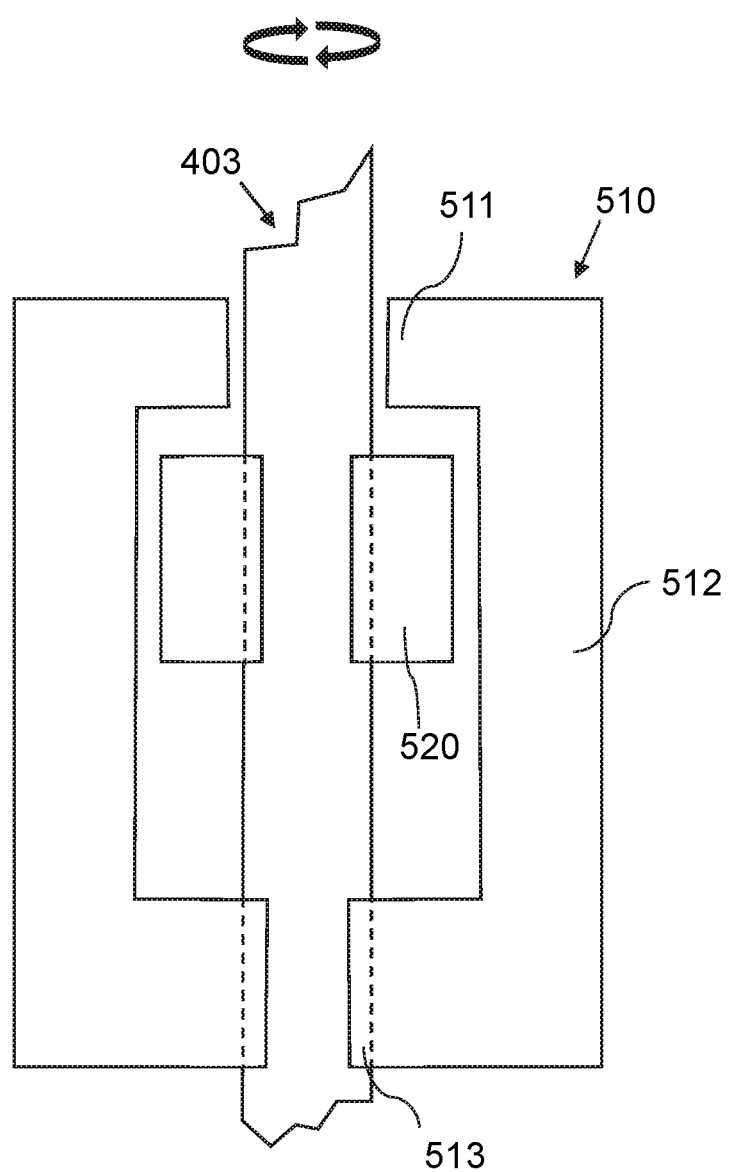
FIG. 5 illustrates a cross-sectional view of an exemplary lifting device according to some embodiments of the present disclosure.

FIG. 5 illustrates a cross-sectional view of an exemplary lifting device 120 according to some embodiments of the present disclosure. As shown, the lifting device 120 may include a shaft assembly 403, a fastening component 520, and a fastening mechanism 510. Dashed lines may represent some portions (e.g., edges) of the lifting device 120 that are invisible or hidden from the view of FIG. 5.

The fastening mechanism 510 may be configured to move an object from a first position to a second position (e.g., from a first height to a second height). For example, the fastening mechanism 510 may be configured to move the loaded object 335 from a first height to a second height as described in FIG. 3. The fastening mechanism 510 may be disposed at one side of the lifting device 120.

The fastening mechanism 510 may include a limiting component 511, a load lifting component 512, and a working component 513, or the like, or a combination thereof. The limiting component 511 provides an example of the limiting component 410. The fastening component 520 provides an example of the safety fastener 470. The load lifting component 512 provides an example of the load lifting mechanism 404. The working component 513 provides an example of the working fastener 490. The working component 513 may be elastically biased against the shaft assembly 403. The limiting component 511 may be located at the top of the lifting device 120. The working component 513 may be spaced from the fastening component 520 by a first distance. The load lifting components 512 may be located at two opposite sides of the lifting device 120. A portion of the load lifting component 512 may be between the fastening component 520 and the working component 513.

In some embodiments, the fastening mechanism 510 may be manufactured as a one-piece component. For example, the load lifting mechanism 404 and the working fastener 470 may be manufactured as a one-piece component. In some embodiments, the fastening mechanism 510 may include separate components assembled together. For example, the limiting component 511, the load lifting component 512, and the working component 513 may be manufactured as a one-piece component. The limiting component 511, the load lifting component 512, and the working component 513 may be manufactured using a single material. As another example, the limiting component 511 and the load lifting component 512 may be manufactured as a one-piece component. Then, the working component 513 may be manufactured as a separate component and may be attached to the load lifting component 512 and the limiting component 511 as part of an installation process. The limiting component 511, the load lifting component 512, and the working component 513 may be made of different materials.

The fastening mechanism 510 may move vertically when the working component 513 engages the shaft assembly 403. The working component 513 may transform the rotation of the shaft assembly 403 into a linear motion of the fastening mechanism 510.

The limiting component 511 may prevent the fastening mechanism 510 from falling when the working component 513 is disconnected from the shaft assembly 403. The fastening mechanism 510 may stop falling when the lower surface of the limiting component 511 touches and receives support from the upper surface of the fastening component 520.

The fastening component 520 may define the moving range of the fastening mechanism 510. The moving range of the fastening mechanism 510 may refer to the moving range of the upper surface of the limiting component 511. The fastening mechanism 510 may be lifted to its highest position when the upper surface of the working component 513 touches the lower surface of the fastening component 520. The fastening mechanism 510 may be descended to its lowest position when the lower surface of the limiting component 511 touches the upper surface of the fastening component 520.

In some embodiments, the fastening component 520 and the shaft assembly 403 may be manufactured together as a one-piece component. The position of the fastening component 520 relative to the position of the shaft assembly 403 may remain the same. In some embodiments, the fastening component 520 may be coupled to the shaft assembly 403. The fastening component 520 may be manufactured as a separate component and attached to the shaft assembly 403 as part of an installation process.

In some embodiments, the position of the fastening component 520 may change relative to the shaft assembly 403.

For example, the fastening component 520 may be a screw. The screw may have helical threads extending over the surface of the screw. The helical threads may be configured to engage with the shaft assembly 403. The shaft assembly 403 may include a shaft 345. The shaft may have a plurality of holes. The plurality of holes may traverse the shaft in the horizontal direction. The plurality of holes may be disposed in different portions of the shaft. For example, hole A (not shown in FIG. 5) of the plurality of holes may be disposed at a height 50 cm from the ground and hole B (not shown in FIG. 5) of the plurality of holes may be disposed at a height 80 cm from the ground. The plurality of holes may be with internal threads. The helical threads of the screw may be complementary to the internal threads of the shaft 345. The screw may be inserted into one of the plurality of holes of the shaft. The position of the fastening component 520 may be changed relatively to the shaft assembly 403 by inserting the screw into different holes. For example, the thickness of the fastening component 520 may be 10 cm. The position of the fastening component 520 may be fixed at 45-55 cm when the fastening component 520 is inserted into the hole A. The position of the fastening component 520 may be fixed at 75-85 cm when the fastening component 520 is inserted into the hole B.

The moving range of the fastening mechanism 510 may be adjusted when the position of the fastening component 520 changes. For example, the moving range of the fastening mechanism 510 may be 60-90 cm when the position of the fastening component 520 is 45-55 cm. The moving range of the fastening mechanism 510 may be 90-120 cm when the position of the fastening component 520 is 45-55 cm.

In some embodiments, the position of the fastening component 520 may remain unchanged relative to the shaft assembly 403. For example, the fastening component 520 may be coupled to the shaft assembly 403 via a glue layer. The glue layer may be applied between the contact surfaces of the fastening component 520 and the shaft assembly 403. As another example, the fastening component 520 may be coupled to the shaft assembly 403 by bonding, welding, etc.

It should be noted that the above description of the embodiments is provided for the purposes of comprehending the present disclosure, and not intended to limit the scope of the present disclosure. For persons having ordinary skills in the art, various variations and modifications may be conducted in the light of the present disclosure. For example, the working component 513 and the load lifting component 512 may be manufactured as a one-piece component. Then, the limiting component 511 may be manufactured as a separate component and be attached to the load lifting component 512 and the working component 513 as part of an installation process. However, those variations and the modifications do not depart from the scope of the present disclosure.

Figure 6:
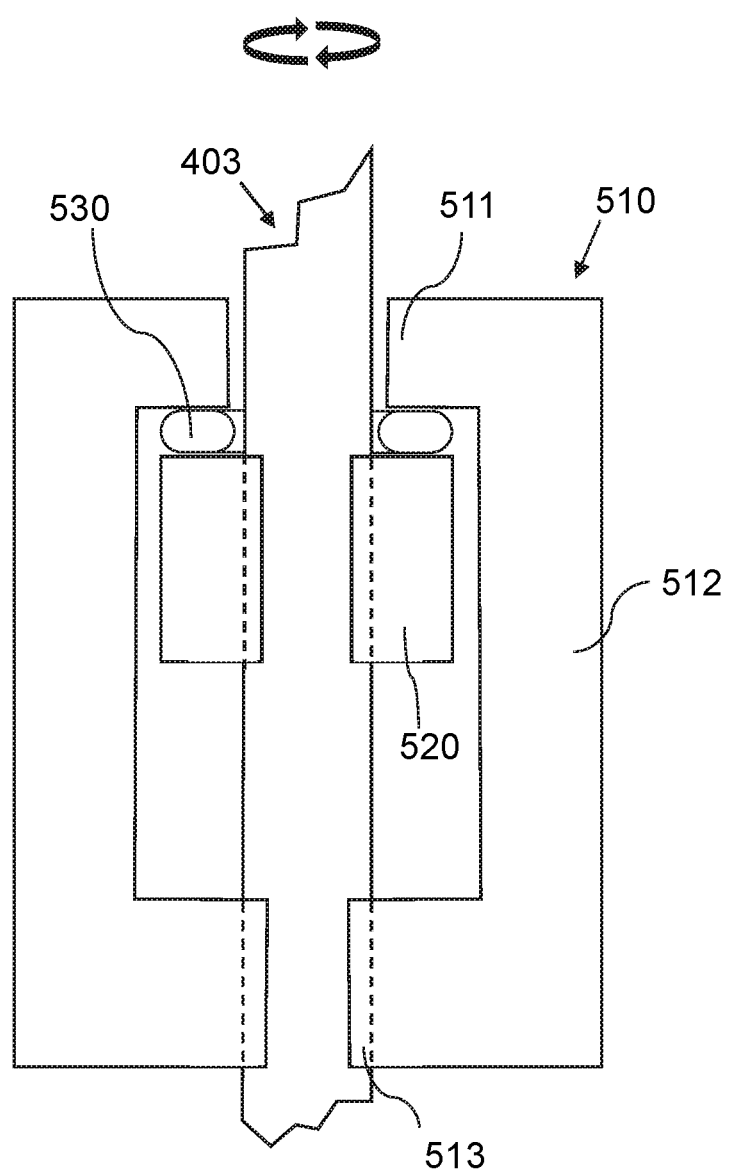
FIG. 6 illustrates a cross-sectional view of an exemplary lifting device according to some embodiments of the present disclosure.

FIG. 6 illustrates a cross-sectional view of an exemplary lifting device 120 according to some embodiments of the present disclosure. As shown, the lifting device 120 may include a shaft assembly 403, a rotating component 530, a fastening component 520, and a fastening mechanism 510. Dashed lines may represent some portions (e.g., edges) of the lifting device 120 invisible or hidden from the view of FIG. 6.

The lifting device 120 illustrated in FIG. 6 is similar to that illustrated in FIG. 5 except for certain features. For instance, the lifting device 120 illustrated in FIG. 6 may further include a rotating component 530. The rotating component 530 may be configured to reduce a rotational resistance. For example, the rotation resistance may be generated when the fastening component 520 rotates with the shaft assembly 403. The rotation resistance may be generated when the fastening mechanism 510 moves toward it lowest position. The upper surface of the fastening component 520 may touch a surface that does not rotate when the fastening mechanism 510 moves to its lowest position. For example, the surface may be the lower surface of the limiting component 511. The rotating component 530 may be configured to reduce a rotational resistance that may be generated between the upper surface of the fastening component 520 and the lower surface of the limiting component 511.

The rotating component 530 may be disposed on the upper surface of the fastening component 520. The upper surface of the rotating component 520 may touch the lower surface of the limiting component 511.

It should be noted that the above description of the embodiments is provided for the purposes of comprehending the present disclosure, and not intended to limit the scope of the present disclosure. For persons having ordinary skills in the art, various variations and modifications may be conducted in the light of the present disclosure. For example, the rotating component 530 may be disposed on the lower surface of the limiting component 511. However, those variations and the modifications do not depart from the scope of the present disclosure.

Figure 7:
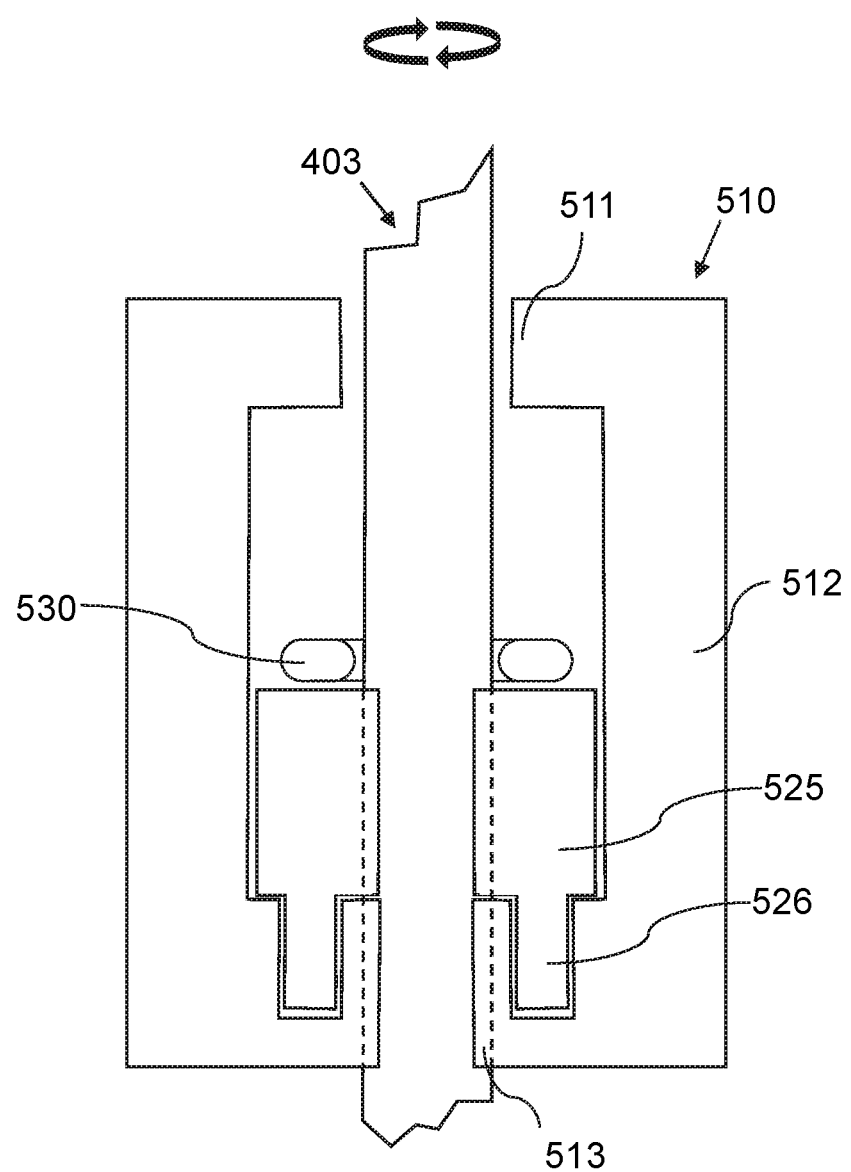
FIG. 7 illustrates a cross-sectional view of an exemplary lifting device according to some embodiments of the present disclosure.

FIG. 7 illustrates a cross-sectional view of an exemplary lifting device 120 according to some embodiments of the present disclosure. As shown, the lifting device 120 may include a shaft assembly 403, a rotating component 530, a fastening component 525 and a fastening mechanism 510. Dashed lines may represent some invisible or hidden edges of the lifting device 120 in the view of FIG. 7.

The fastening component 525 may be configured to prevent the fastening mechanism 510 from falling. The fastening component 525 may include a protrusion 526. The protrusion 526 may be inserted into a hole in the fastening mechanism 510. The hole may be in the working component 513. The circumferential movement of the fastening component 525 may be confined when the protrusion 526 is in the hole. The fastening component 525 may move with the working component 513 when the circumferential movement is confined.

The protrusion 526 may move out of the hole when the working component 513 is disengaged from the shaft assembly 403. The restriction on the circumferential movement of the fastening component 525 may be removed when the protrusion 526 is out of the hole. The fastening component 525 may rotate with the shaft assembly 403.

The fastening mechanism 510 may fall when the working component 513 disengages from the shaft assembly 403. The fastening component 525 may remain immobile in the vertical direction when the fastening mechanism 510 falls. The lower surface of the limiting component 511 may touch the upper surface of the rotating component 530 when the fastening mechanism 510 falls to its lowest position. A rotation resistance may be generated between the limiting component 511 and the fastening component 525. The rotation component 530 may be configured to reduce the rotation resistance.

It should be noted that the above description of the embodiments is provided for the purposes of comprehending the present disclosure, and not intended to limit the scope of the present disclosure. For persons having ordinary skills in the art, various variations and modifications may be conducted in the light of the present disclosure. For example, there may be a buffer component between the limiting component 511 and the fastening component 525. However, those variations and the modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system comprising:
a working assembly including a working fastener;
a safety assembly including a safety fastener;
a shaft assembly; and
a load lifting mechanism including a first fastener surface, wherein:
the working assembly is configured to support the load lifting mechanism when the working assembly is coupled to the load lifting mechanism;
the safety assembly is configured to prevent the load lifting mechanism from falling when the working assembly fails;
a first connecting portion of the working fastener is connected to the shaft assembly, and a first fastener portion of the working fastener is connected to the first fastener surface;
a second connecting portion of the safety fastener is connected to the shaft assembly; and
when the working assembly fails, the safety fastener moves along a direction pointing from the working fastener to the safety fastener and a distance between the safety fastener and the working fastener increases.

2. The system of claim 1, wherein the load lifting mechanism further includes a second fastener surface and the safety fastener is connected to the load lifting mechanism at the second fastener surface.

3. The system of claim 2, wherein the load lifting mechanism further includes a countersink on the second fastener surface.

4. The system of claim 3, wherein the load lifting mechanism further includes a locking component, wherein
the locking component is in the countersink when the safety fastener is connected to the load lifting mechanism at the second fastener surface; and
the locking component is out of the countersink when the safety fastener is disconnected from the load lifting mechanism and the working fastener is disengaged from the shaft assembly.

5. The system of claim 4, wherein the safety fastener further includes a limiting component and an adapter, and the adapter includes a first contact surface and a second contact surface, wherein
the first contact surface is connected to the limiting component at a top surface of the limiting component that is opposite to the second fastener surface; and
the second contact surface is connected to a second fastener portion of the safety fastener.

6. The system of claim 5, wherein the safety assembly further includes a rotating component, and the first contact surface is connected to the limiting component through the rotating component at the top surface of the limiting component.

7. The system of claim 5, wherein the safety assembly further includes an elastic component, wherein
the elastic component is connected to the second fastener portion; and
the elastic component is located between the adapter and a protruding portion of the locking component.

8. The system of claim 1, further comprises a driving device, wherein the driving device includes a motor and a gearbox, and the gearbox is coupled to the shaft assembly.

9. The system of claim 1, wherein the working fastener is configured to drive the load lifting mechanism to move along the shaft assembly when the working fastener is engaged with the shaft assembly.

10. The system of claim 1, wherein the safety fastener is configured to support the load lifting mechanism when the working fastener is disengaged from the shaft assembly.

11. A lifting equipment comprising:
a working assembly including a working fastener;
a safety assembly including a safety fastener;
a shaft assembly; and
a load lifting mechanism; wherein
a first connecting portion of the working fastener is connected to the shaft assembly, and a first fastener portion of the working fastener is connected to the load lifting mechanism;
a second connecting portion of the safety fastener is connected to the shaft assembly; and
when the working assembly fails, the safety fastener moves along a direction pointing from the working fastener to the safety fastener and a distance between the safety fastener and the working fastener increases.

12. The lifting equipment of claim 11, wherein
the working assembly is configured to support the load lifting mechanism when the working assembly is coupled to the load lifting mechanism; and
the safety assembly is configured to prevent the load lifting mechanism from falling when the working assembly fails.

13. The lifting equipment of claim 11, wherein the first fastener portion of the working fastener is connected to the load lifting mechanism at a first fastener surface of the load lifting mechanism, and the load lifting mechanism further includes a second fastener surface and the safety fastener is connected to the load lifting mechanism at the second fastener surface.

14. The lifting equipment of claim 13, wherein the load lifting mechanism further includes a countersink and a locking component, wherein
the countersink is on the second fastener surface;
the locking component is in the countersink when the safety fastener is connected to the load lifting mechanism at the second fastener surface; and
the locking components is out of the countersink when the safety fastener is disconnected from the load lifting mechanism and the working fastener is disengaged from the shaft assembly.

15. The lifting equipment of claim 11, wherein the working fastener is configured to drive the load lifting mechanism to move along the shaft assembly when the working fastener is engaged with the shaft assembly.

16. The lifting equipment of claim 11, wherein the safety fastener is configured to support the load lifting mechanism when the working fastener is disengaged from the shaft assembly.

17. The lifting equipment of claim 11, wherein the safety fastener further includes a limiting component and an adapter, and the adapter includes a first contact surface and a second contact surface, wherein
the first contact surface is connected to the limiting component at a top surface of the limiting component; and
the second contact surface is connected to a second fastener portion of the safety fastener.

18. The lifting equipment of claim 17, wherein the safety assembly further includes a rotating component, the first contact surface is connected to the limiting component through the rotating component at the top surface of the limiting component.

19. The lifting equipment of claim 17, wherein the safety assembly further includes an elastic component, wherein
the elastic component is connected to the second fastener portion; and
the elastic component is located between the adapter and a protruding portion of the locking component.

20. A C-arm medical device comprising:
a lifting device, a C-arm frame, a radiation source, and a detector, wherein
the lifting device is configured to support the C-arm frame; and
the C-arm frame is configured to support the radiation source and detector, wherein the lifting device comprises:
a working assembly including a working fastener;
a safety assembly including a safety fastener;
a shaft assembly; and
a load lifting mechanism, wherein
a first connecting portion of the working fastener is connected to the shaft assembly, and a first fastener portion of the working fastener is connected to the load lifting mechanism;
a second connecting portion of the safety fastener is connected to the shaft assembly.

* * * * *